United States Patent
Elliott

(10) Patent No.: US 9,080,965 B2
(45) Date of Patent: Jul. 14, 2015

(54) SENSOR ASSEMBLIES

(75) Inventor: Howard Elliott, Oxfordshire (GB)

(73) Assignee: Future Technology (Sensors) Ltd, Oxfordshire (GB)

( * ) Notice: Subject to any disclaimer, the term of this patent is extended or adjusted under 35 U.S.C. 154(b) by 616 days.

(21) Appl. No.: 13/508,141

(22) PCT Filed: Oct. 25, 2010

(86) PCT No.: PCT/GB2010/001971
§ 371 (c)(1),
(2), (4) Date: Jul. 6, 2012

(87) PCT Pub. No.: WO2011/061471
PCT Pub. Date: May 26, 2011

(65) Prior Publication Data
US 2012/0260733 A1    Oct. 18, 2012

(30) Foreign Application Priority Data
Nov. 20, 2009 (EP) .................................... 09014479

(51) Int. Cl.
*G01D 11/24* (2006.01)
*G01N 27/407* (2006.01)

(52) U.S. Cl.
CPC ....... *G01N 27/4078* (2013.01); *Y10T 29/49002* (2015.01)

(58) Field of Classification Search
None
See application file for complete search history.

(56) References Cited

U.S. PATENT DOCUMENTS

| | | | | |
|---|---|---|---|---|
| 3,791,953 A | * | 2/1974 | Minushkin et al. | 204/410 |
| 4,309,897 A | * | 1/1982 | Springer et al. | 73/23.31 |
| 2005/0103113 A1 | | 5/2005 | Ernsberger et al. | |
| 2010/0186489 A1 | * | 7/2010 | Burrows et al. | 73/114.19 |

FOREIGN PATENT DOCUMENTS

DE    10 2007 018 001 A1    10/2008

* cited by examiner

*Primary Examiner* — Robert R Raevis
(74) *Attorney, Agent, or Firm* — Kilyk & Bowersox, P.L.L.C.

(57) ABSTRACT

The invention relates to a sensor assembly. The assembly includes a sensor body 2 of appropriate construction (preferably substantially ceramic) with a radial flange 8. A housing 20 is of two-part integral construction and includes an annular groove or recess in which the radial flange 8 of the sensor body 2 is received when the sensor assembly is in its assembled form. The annular groove is defined by a pair of facing shoulders 28, 36 each having an annular surface 30, 38 and a substantially cylindrical surface 32, 40. The annular surfaces 30, 38 are in sliding contact with the flange 8 and apply a compressive load to the flange to form a hermetic seal between the housing 20 and the sensor body 2. The hermetic seal is maintained even if the sensor assembly is used at high operating temperatures.

15 Claims, 3 Drawing Sheets

SENSOR ASSEMBLIES

TECHNICAL FIELD

The present invention relates to sensor assemblies, and in particular to sensor assemblies that incorporate a ceramic body and can be used in high temperature operating environments.

The term "sensor assemblies" is intended to cover a wide variety of different sensor types and products as illustrated by the following (non-exhaustive) list: pressure sensors, strain gauge sensors, temperature sensors, capacitive sensors, displacement measurement sensors, blade tip timing sensors, blade tip clearance measurement sensors, inductive sensors, optical sensors and microwave sensors and infra-red sensors.

A further range of suitable products include electromagnetically transparent windows which are used to protect electromagnetically-based systems from the high temperature and pressure experienced in a gas turbine environment, for example. These windows can be made from materials such as sapphire, quartz and diamond, as well as more conventional ceramic materials. The term "transparent" is intended to refer to any materials which do not impede the path of the electromagnetic radiation to any significant degree. Such materials are usually chosen for use with specific measurement systems which incorporate optical, microwave or infra-red technology, for example.

BACKGROUND ART

Known sensor assemblies typically comprise composite ceramic/metal components that are brazed together using conventional brazing techniques. Such a known sensor assembly might include a metal housing with a metallised aluminium oxide bush brazed into the inner diameter of the housing. A sensor body is then brazed into the internal diameter of the bush.

The sensor body can be made of one or more layers of metal, electrically conductive ceramic, electrically non-conductive ceramic that is made conductive by having a layer of conductive material (e.g. a metal) deposited on its surface, or a conductive ceramic/metal composite, for example. Conductive layers can define electrodes or other sensing elements or shield layers. Non-conductive layers can define insulating spacers that are positioned between conductive layers. The layers that form the sensor body can be machined as a preformed part and then bonded to an adjacent layer or deposited on an adjacent layer using any suitable deposition technique. If the outer layer of the sensor body is made substantially from a ceramic material then its outer surface can be metallised so that the sensor body can be brazed directly into the housing using conventional brazing techniques without the need for the intermediate bush.

The metal housing parts of the sensor assembly might be manufactured from a low expansion alloy which is specifically designed to have a coefficient of thermal expansion substantially similar to that of the bush and/or the sensor body. If the sensor assembly is exposed to high temperatures during operation then the housing, bush and sensor body all expand at similar rates to minimise the thermal stress between the individual components.

One problem with the use of low expansion alloys is that they tend to oxidise at temperatures approaching 500° C. This places an upper limit on the operating temperature of the sensor assembly. It can be difficult to find a metal that is suitable for use at higher temperatures and which also has a thermal expansion coefficient that is substantially similar to that of the bush and/or the sensor body. A known solution is to use so-called "active braze" techniques which allow certain ceramic materials to be brazed to metals without the need for metallised coatings and also provide a degree of compliance between the two different materials to accommodate the different rates of thermal expansion. In practice, however, the operating temperature of active braze alloys is limited to about 800° C. which is still not sufficiently high for certain operations. The compliant coatings that are needed to provide the degree of compliance also tend to oxidise at temperatures below 500° C. and it is normally necessary to provide a hermetic seal at the braze interface to minimise the oxidation effect when the operating temperature falls below this threshold.

Further problems are known to exist in situations where large relative movements occur between the component parts of the sensor assembly as a result of thermal expansion. Large relative movement can only be accommodated by increasing the thickness of the complaint coatings and this can place practical limitations on the design of the sensor assembly.

SUMMARY OF THE INVENTION

The present invention provides a sensor assembly comprising: a sensor body having a radial flange; and a housing having an annular groove in which the radial flange of the sensor body is received, the annular groove being defined by a pair of facing shoulders each having an annular surface and a substantially cylindrical surface; wherein the annular surfaces of the shoulders are in sliding contact with annular surfaces of the flange and apply a compressive load to the flange.

The sensor body is not physically secured to the housing (e.g. by brazing) but is firmly held within the housing as a result of the compressive load that is applied to the flange by the annular surfaces of the shoulders. The particular construction of the sensor assembly means that there are no significant problems with differential thermal expansion and the sensor assembly is therefore inherently suitable for high temperature operation. The sensor assembly can be manufactured in a cost-effective manner using conventional brazing techniques as described in more detail below.

The sensor body is preferably formed substantially from a ceramic material and can include one or more electrically conductive layers and one or more electrically non-conductive layers, for example. The precise shape and construction of the sensor body is not a critical feature of the present invention and will depend on the type of sensor assembly. The sensor body must, however, include the radial flange.

The housing is preferably a two-part housing formed from a high temperature metal. More particularly, one of the facing shoulders is preferably formed in a first housing part and the other of the facing shoulders is preferably formed in a second housing part. The first and second housing parts are secured together to form the two-part housing in such a way that the shoulders are in register and define the annular groove into which the radial flange of the sensor body is received. The flange is therefore normally held between the two housing parts by the applied compressive load.

The first housing part is preferably brazed to the second housing part by a braze material. Any suitable braze material can be used.

The sliding contact between the housing and the annular surfaces of the flange under the compressive load preferably provides a hermetic seal between the housing and the sensor body. The hermetic seal is maintained even when the sensor assembly is exposed to high operating temperatures.

The present invention provides a method of manufacturing a sensor assembly comprising the steps of: providing a sensor body having a radial flange; locating the sensor body in a two-part housing having an annular groove in which the radial flange of the sensor body is received, the annular groove being defined by a pair of facing shoulders each having an annular surface and a substantially cylindrical surface, one shoulder being formed in a first housing part and another shoulder being formed in a second housing part; bringing the annular surfaces of the shoulders into contact with the annular surfaces of the flange; and brazing the first and second housing parts together to form an integral two-part housing by (i) raising the sensor assembly to a particular brazing temperature during which the first and second housing parts undergo thermal expansion, (ii) applying a braze material to the first and second housing parts in a molten state, and (iii) reducing the temperature of the sensor assembly so that the braze material solidifies to secure the first and second housing parts together to form the integral two-part housing and during which the first and second housing parts undergo thermal contraction to apply a compressive load to the flange.

In a preferred method the first and second housing parts are assembled together to substantially surround the sensor body with respective brazing surfaces in contact or in close proximity. During the brazing process, as the sensor assembly is raised to a particular brazing temperature, the first and second housing parts are preferably loaded to maintain direct contact between the annular surfaces of the facing shoulders and the annular surfaces of the flange. More particularly, the annular surfaces of the shoulders are preferably brought into contact with the annular surfaces of the flange by applying a loading which forces the first and second housing parts towards each other in the axial direction. At the particular brazing temperature, the braze material is in the molten state and the contact between the first and second housing parts and the flange is preferably maintained under load. The brazing material is applied between the brazing surfaces of the first and second housing parts. The braze material is typically applied when the sensor assembly is at an ambient temperature (i.e. in "cold" application process) so that it transitions to the molten state when the temperature of the sensor assembly reaches the particular brazing temperature, but the braze material can also be applied once the temperature of the sensor assembly has reached the brazing temperature (i.e. in a "hot" application process). As the temperature of the sensor assembly is subsequently reduced, the braze material solidifies to fixedly secure the first and second housing parts together to form an integral two-part housing surrounding the sensor body, which is typically made substantially of ceramic material. The first and second housing parts undergo thermal contraction and effectively shrink onto the flange of the sensor body to apply a significant compressive load onto the flange in the axial direction. In other words, the housing contracts more than the sensor body as the temperature decreases. The application of the compressive load results in the creation of a hermetic seal between the housing and the sensor body. Providing a hermetic seal is important because it prevents moisture from penetrating the sensor assembly and reducing its operational performance.

It will be readily appreciated that the compressive load that arises from the shrinkage of the first and second housing parts is different to the external loading that is applied during the brazing process and is maintained throughout the operating lifetime of the sensor assembly. Ceramic materials are known to cope well with compressive loads and assessment shows that the risk of damage to the sensor body during the brazing process is very low. In practice the compressive load applied when the sensor assembly is at a high operating temperature will be slightly less than for ambient temperature because of the differential thermal expansion between the housing and the sensor body in the axial direction. However, the compressive load will always be at a sufficient level to maintain the hermetic seal.

When the sensor assembly is used at a high operating temperature the housing undergoes thermal expansion and expands away from the sensor body in the radial direction. In other words, the housing expands more than the sensor body as the temperature increases. The expansion causes the annular surfaces of the housing to slide relative to the annular surfaces of the flange in the radial direction and this sliding contact may be promoted by a suitable choice of material for the sensor body (or its contact surfaces) and/or the housing. Any movement of the housing relative to the sensor body in the axial direction is very small (typically in the order of a few microns) and is accommodated by the material properties of the housing.

The maximum operating temperature of the sensor assembly is effectively limited by the brazing temperature, taking into account the mechanical properties of the braze material and the housing material etc. It is expected that for typical brazing temperatures in excess of 1200° C. then the sensor assembly can function properly at temperatures approaching 1000° C. at the brazing surfaces. It will be readily appreciated that the temperature at other parts of the sensor assembly removed from the brazing surfaces may be significantly higher. For example, in the case of a capacitive sensor that is used to measure the clearance between the tip of a gas turbine engine blade and the surrounding casing then the front face of the sensor assembly might be exposed to temperatures of about 1500° C. with a cooler temperature being experienced at the rear of the sensor assembly where the brazing surfaces are located.

DRAWINGS

Figure 1:
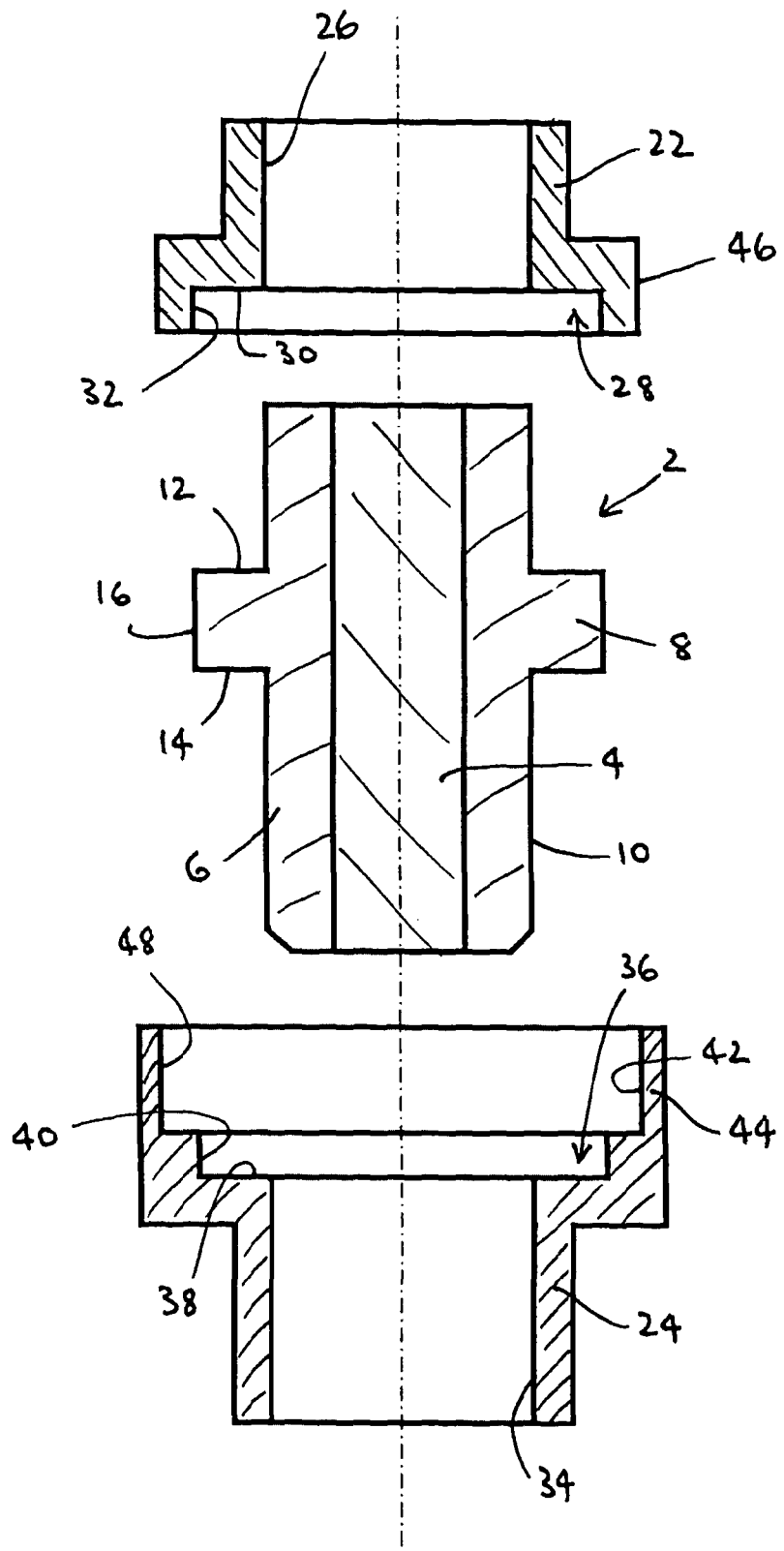
FIG. 1 is an exploded cross section diagram showing a sensor assembly according to the preset invention.
Figure 2:
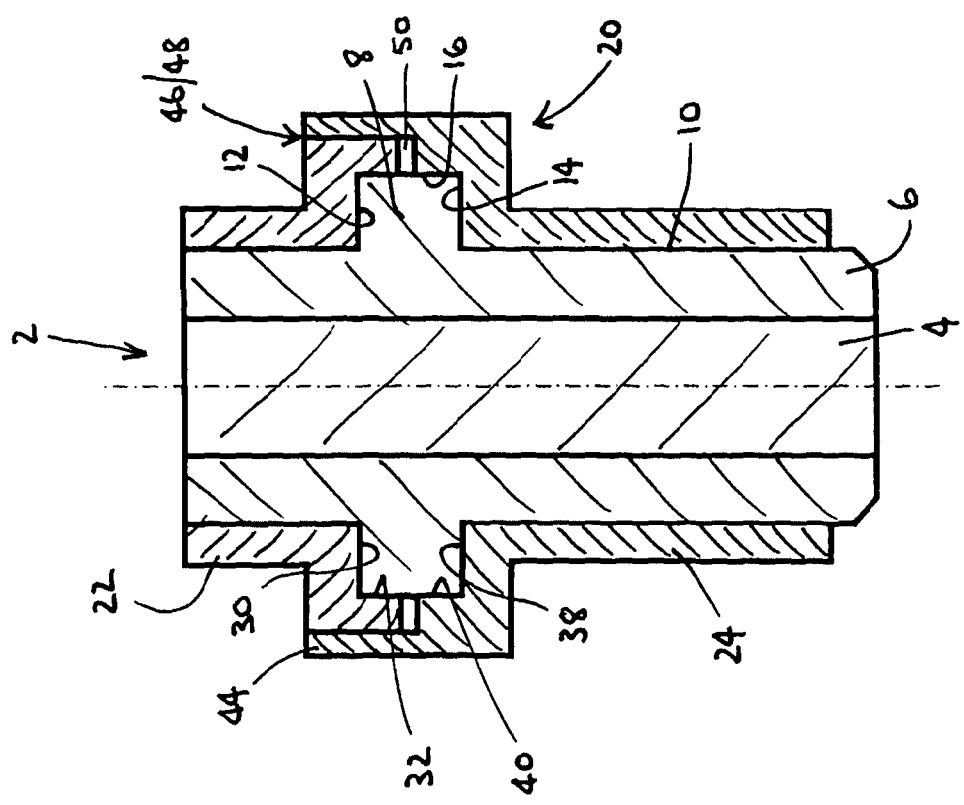
FIG. 2 is a cross section diagram showing the complete sensor assembly at an ambient temperature.

FIGS. 1 and 2 show a sensor assembly with a sensor body 2 that is made of ceramic material and an integral two-part metal housing 20.

The sensor body 2 includes an electrode 4 formed from electrically conductive ceramic and an outer layer 6 formed from electrically non-conductive ceramic which acts as an insulating layer. The outer layer 6 can be deposited on, or bonded to, the inner electrode 4 using any suitable manufacturing technique such that the sensor body 2 is an integral structure. The different ceramic materials that are used to form the electrode 4 and the outer layer 6 can be selected to have substantially similar thermal expansion coefficients. It will be readily appreciated that the sensor body 2 may have any convenient or suitable construction depending on the type of sensor with one or more layers of metal, electrically conductive ceramic, electrically non-conductive ceramic that is made conductive by having a layer of conductive material (e.g. a metal) deposited on its surface, or a conductive ceramic/metal composite, for example.

The sensor body 2 includes a flange 8 that protrudes radially outwardly from the outer cylindrical surface 10 of the outer layer 6. The flange 8 includes a first annular surface 12, a second annular surface 14 and a cylindrical surface 16.

The housing 20 is made up of a first housing part 22 and a second housing part 24.

The first housing part 22 includes a central cylindrical bore 26 and an annular shoulder 28 having a larger diameter than the central bore and which is defined by an annular surface 30 and a cylindrical surface 32.

The second housing part 24 includes a central cylindrical bore 34 and an annular shoulder 36 having a larger diameter than the central bore and which is defined by an annular surface 38 and a cylindrical surface 40. An outer bore 42 has a larger diameter than the cylindrical surface 40 and is defined by an axially extending flange 44 of the second housing part.

The central bores 26, 34 in each housing part are sized to receive the sensor body 2 with a close tolerance fit to the outer surface 10 when the sensor assembly is at an ambient temperature. However, the radial fit between the outer surface of the sensor body flange and the inner surface of the housing is generally not considered to be critical.

The first housing part 22 includes a cylindrical brazing surface 46. When the first housing part 22 is assembled to the second housing part 24 as shown in FIG. 2 then the brazing surface 46 faces a corresponding cylindrical brazing surface 48 of the flange 44. More particularly, when assembled together, the brazing surface 46 of the first housing part 22 is located radially within the flange 44 of the second housing part 24 with a close tolerance fit. The annular shoulders 28, 36 are also aligned to define an annular groove or recess into which the flange 8 of the sensor body 2 is received with a close tolerance fit when the sensor assembly is at an ambient temperature. Although not shown, the upper surfaces of the first and second housing parts 22, 24 may be chamfered adjacent the respective brazing surface so that they when they are assembled together they define a narrow annular groove into which the brazing material can be deposited.

The assembly steps of the sensor assembly will now be explained with reference to FIGS. 3A and 3B.

The second housing part 24 is supported in a suitable frame or support S. The sensor body 2 is inserted into the central cylindrical bore 34 of the second housing part 24 and the first housing part 22 is then located to the second housing part 24 with the upper part of the sensor body 2 positioned in the central cylindrical bore 26 and the respective brazing surfaces 46, 48 axially aligned as shown in FIG. 3A.

The first and second housing parts 22, 24 are then secured together by a brazing process. A brazing material BM (optionally in the form of a paste) is applied to the upper surface of the sensor assembly at the interface between the respective brazing surfaces 46, 48 of the first and second housing parts 22, 24. The brazing material may sit in the narrow annular groove (not shown) mentioned above. The sensor assembly is raised to a particular brazing temperature that is determined by the brazing material that it to be used. During the brazing process, an axial loading is applied to the first housing part 22 (as indicated by the arrows) to maintain a direct contact between the annular surfaces 30, 38 of the facing shoulders and the annular surfaces 12, 14 of the flange 8.

Figure 3B:
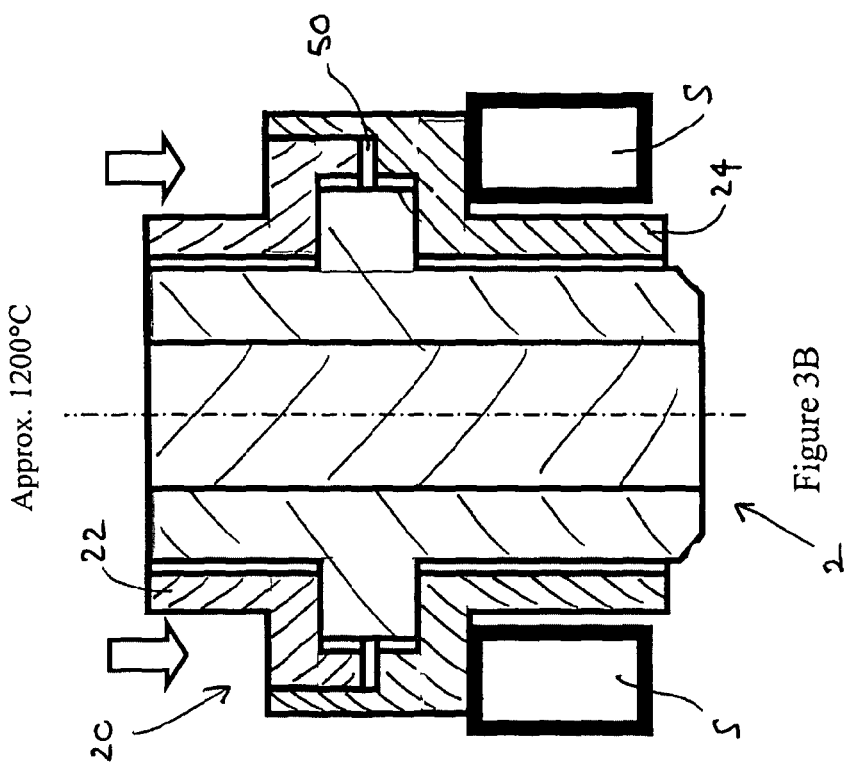
FIGS. 3A and 3B are cross section diagrams showing the brazing process by which the two parts of the housing of the sensor assembly are secured together to surround the inner sensor body.
Figure 3A:
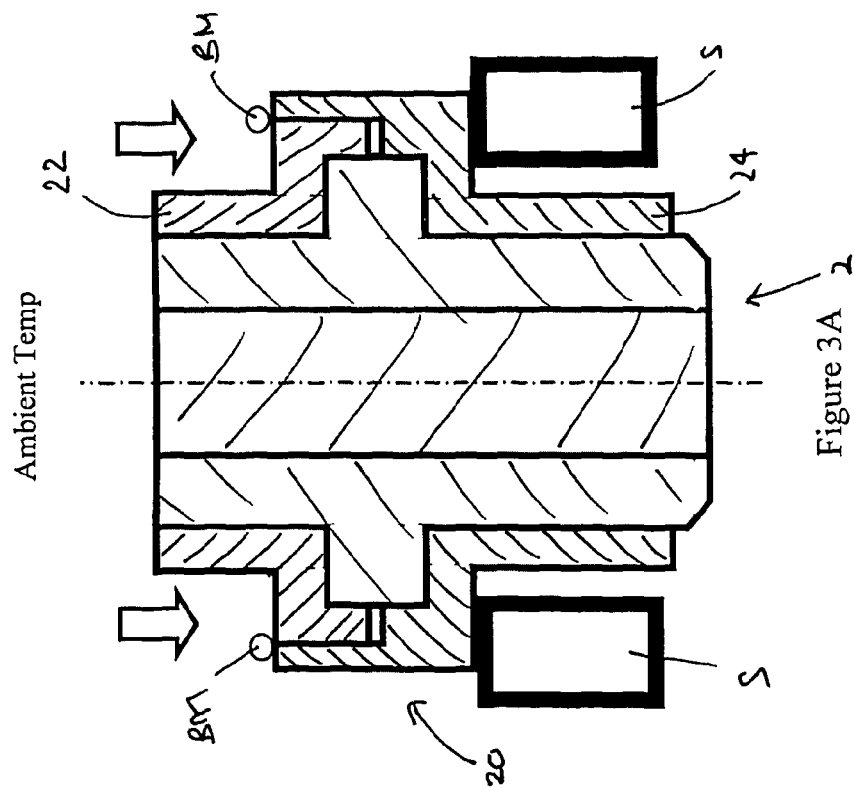

As the temperature of the sensor assembly is raised to the brazing temperature, the first and second housing parts 22, 24 expand away from the sensor body 2 in the radial direction as shown in FIG. 3B. Expansion of the first and second housing parts 22, 24 in the axial direction is limited and direct contact between the annular surfaces 30, 38 of the facing shoulders and the annular surfaces 12, 14 of the flange 8 is maintained by the axial loading. The axial gap 50 ensures that there is no direct contact between the first and second housing parts 22, 24 that would otherwise limit or restrict the amount of axial loading that can be applied to the flange 8. In other words, the axial compression force acting on the annular surfaces 12, 14 of the flange 8 is determined solely by the axial loading applied during the brazing process and the subsequent compressive load.

Once the temperature of the sensor assembly reaches the brazing temperature, the braze material is in the molten state and is drawn down into the interface between the brazing surfaces 46, 48 of the first and second housing parts 22, 24 by a capillary action.

As the temperature of the sensor assembly is subsequently reduced, the braze material solidifies to secure the first and second housing parts 22, 24 together to form an integral two-part housing 20 surrounding the sensor body 2. More particularly, the first and second housing parts 22, 24 are fixedly secured together by the brazing material at the join or interface between the facing brazing surfaces 46, 48. The first and second housing parts 22, 24 are not secured together at any other interface and are not secured in any way to the sensor body 2. The absence of fixing between the housing 20 and the sensor body 2 means that the sensor assembly does not experience any stresses as a result of differential thermal expansion which might in other circumstances lead to the disintegration or failure of the ceramic and/or metal components.

The first and second housing parts 22, 24 undergo thermal contraction and effectively shrink onto the flange 8 of the sensor body 2 to apply a significant compressive load onto the flange in the axial direction. The application of the compressive load during the brazing process results in the creation of a hermetic seal between the housing 20 and the sensor body 2. More particularly, the hermetic seal is formed between the annular surfaces 30, 38 of the facing shoulders and the annular surfaces 12, 14 of the flange 8. One or more of the annular surfaces may be machined, coated or otherwise treated to provide a smooth surface finish so that close physical contact is established across as large an area as possible.

Figure 4:
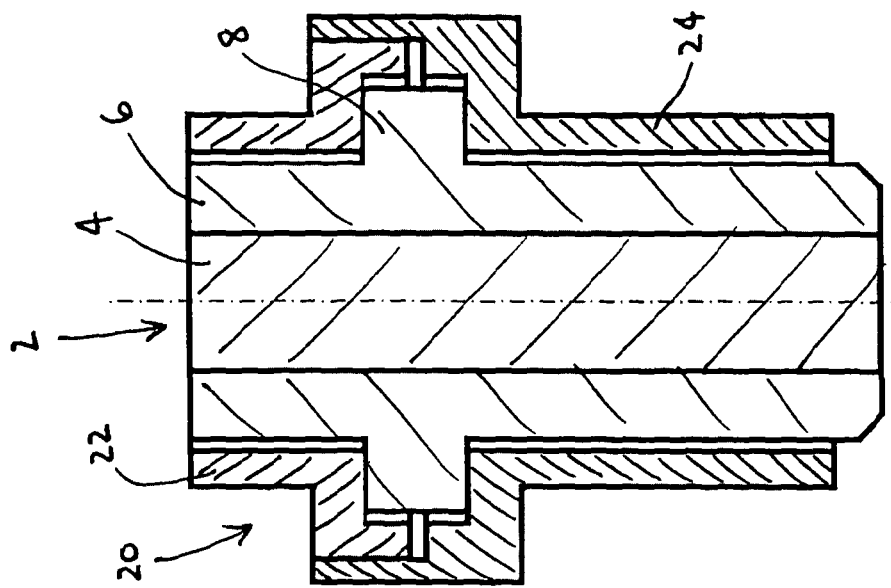
FIG. 4 is a cross section diagram showing the complete sensor assembly of FIG. 2 at a high operating temperature.

When the sensor assembly is used at a high operating temperature the first and second housing parts 22, 24 undergo thermal expansion and expand away from the sensor body 2 in the radial direction as shown in FIG. 4. The expansion causes the annular surfaces 30, 38 of the housing to slide relative to the annular surfaces 12, 14 of the flange 8 in the radial direction. However, the flange 8 of the sensor body 2 remains under a compressive load at the high operating temperature and the hermetic seal is maintained at all times during the operational lifetime of the sensor assembly.

The thickness of the flange 8 in the axial direction is preferably kept to a minimum in order to minimise the differential thermal expansion between the flange and the first and second housing parts 22, 24. It will be readily appreciated that if the differential thermal expansion is too large then this might result in the hermetic seal being compromised. However, the flange 8 must also be thick enough to cope with the external loading that is applied during the brazing process and the resulting compression load. The flange 8 also preferably protrudes beyond the outer surface of the sensor body 2 by an amount that will allow radial expansion of the first and second housing parts 22, 24 away from the sensor body while keeping sufficient contact between the respective annular surfaces to maintain the hermetic seal.

The invention claimed is:

1. A sensor assembly comprising:
a sensor body formed substantially from a ceramic material and defining a flange that extends radially outwardly and comprises first and second annular surfaces; and
a housing having an annular groove in which the flange is received, the annular groove being defined by a pair of facing shoulders each having an annular surface and a substantially cylindrical surface;
wherein the annular surfaces of the shoulders are in sliding contact with the annular surfaces of the flange and apply a compressive load to the flange in opposing axial directions.

2. The sensor assembly of claim 1, wherein the housing is a two-part housing.

3. The sensor assembly of claim 2, wherein one of the facing shoulders is formed in a first housing part and the other of the facing shoulders is formed in a second housing part.

4. The sensor assembly of claim 3, wherein the first housing part is secured to the second housing part.

5. The sensor assembly of claim 3, wherein the first housing part is brazed to the second housing part by a braze material.

6. The sensor assembly of claim 1, wherein the sensor body is not fixed to the housing.

7. The sensor assembly of claim 1, wherein the sliding contact between the housing and the annular surfaces of the flange under the compressive load provides a hermetic seal between the housing and the sensor body.

8. The sensor assembly of claim 1, wherein the sensor body comprises an electrically conductive electrode and an outer layer of a ceramic, and the flange is made of the ceramic.

9. The sensor assembly of claim 8, wherein the ceramic is an electrically non-conductive ceramic.

10. The sensor assembly of claim 1, wherein the annular surfaces of the shoulders apply a compressive load sufficient to maintain a hermetic seal between the sensor body and the housing in the absence of any external loading applied to the housing.

11. A method of manufacturing a sensor assembly comprising the steps of:
providing a sensor body formed substantially from a ceramic material and defining a flange that extends radially outwardly and comprises first and second annular surfaces;
locating the sensor body in a two-part housing having an annular groove in which the flange of the sensor body is received, the annular groove being defined by a pair of facing shoulders each having an annular surface and a substantially cylindrical surface, one shoulder being formed in a first part of the two-part housing and the other shoulder being formed in a second part of the two-part housing;
bringing the annular surfaces of the shoulders into contact with the annular surfaces of the flange under conditions that cause the shoulders to apply a compressive load to the flange; and
brazing the first and second parts of the two-part housing together to form an integral two-part housing by (i) raising the sensor assembly to a particular brazing temperature during which the first and second housing parts undergo thermal expansion, (ii) applying a braze material to the first and second housing parts in a molten state, and (iii) reducing the temperature of the sensor assembly so that the braze material solidifies to secure the first and second housing parts together to form the integral two-part housing, wherein the first and second housing parts undergo thermal contraction to apply a compressive load to the flange and form a hermetic seal between the sensor body and the integral two-part housing.

12. The method of making a sensor assembly of claim 11, wherein the annular surfaces of the shoulders are brought into contact with the annular surfaces of the flange by applying a loading which forces the first and second housing parts towards each other.

13. The method of claim 11, wherein the sensor body comprises an electrically conductive electrode and an outer layer of a ceramic, and the flange is made of the ceramic.

14. The method of claim 13, wherein the ceramic is an electrically non-conductive ceramic.

15. The method of claim 11, wherein, after the step of reducing the temperature, the annular surfaces of the shoulders apply a compressive load sufficient to maintain a hermetic seal between the sensor body and the housing in the absence of any external loading applied to the housing.

* * * * *